United States Patent [19]

Nakamura et al.

[11] 4,177,141

[45] Dec. 4, 1979

[54] FILTER MEDIUM, PROCESS FOR PREPARATION THEREOF, FILTERING METHOD AND FILTERING APPARATUS

[76] Inventors: Akio Nakamura, 4-6, Inohana 3; Hirosi Isizuka, 48, Minato-cho, both of Chiba City, Chiba Pref., Japan

[21] Appl. No.: 891,919

[22] Filed: Mar. 30, 1978

[51] Int. Cl.² .............................................. B01D 37/02
[52] U.S. Cl. .......................................... 210/70; 210/75
[58] Field of Search ................. 210/65, 483, 484, 496, 210/499, 500 R, 506, 507, 508, 509, 510, 503, 504, 505, 70, 75, 79, 81

[56] References Cited

U.S. PATENT DOCUMENTS

| 1,910,771 | 5/1933 | Knight | 210/496 |
| 2,672,214 | 3/1954 | Goodloe | 210/496 |

FOREIGN PATENT DOCUMENTS

| 50-80067 | 1/1975 | Japan . |
| 50-13167 | 7/1975 | Japan . |
| 50-38674 | 9/1975 | Japan . |
| 50-41968 | 9/1975 | Japan . |

Primary Examiner—Frank Sever

Attorney, Agent, or Firm—Armstrong, Nikaido, Marmelstein & Kubovcik

[57] ABSTRACT

A filter medium comprising a body of the filter medium having the space thereof partitioned three-dimensionally, irregularly and manifoldly by bent linear members having a strength sufficient to cause substantially no substantial deformation when the filter medium is actually used, and an effluent pipe connected to the body of the filter medium, said effluent pipe having an opening located in the interior of the body, from which a filtrate flows out, is disclosed. When at least one component is filtered or separated from a material to be treated by filtrate the dispersion medium as the filtrate is interposed between a filter cake and the surface portion of the body of the filter medium and the dispersion medium as the filtrate is allowed to pass very easily through the filter cake. Accordingly, clogging is not caused in the filter medium and the filtration can be performed at a substantially uniform flow rate throughout the operation. In addition, a process for the preparation of such filter medium and a filtering method and apparatus using such filter medium are provided. This filter medium can be effectively used in any field for separating components from dispersions, for example, separating oils from water.

7 Claims, 21 Drawing Figures

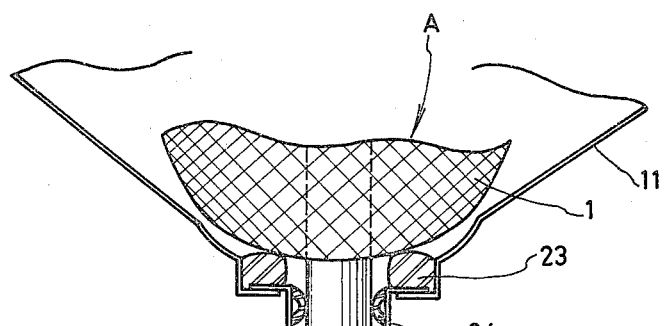
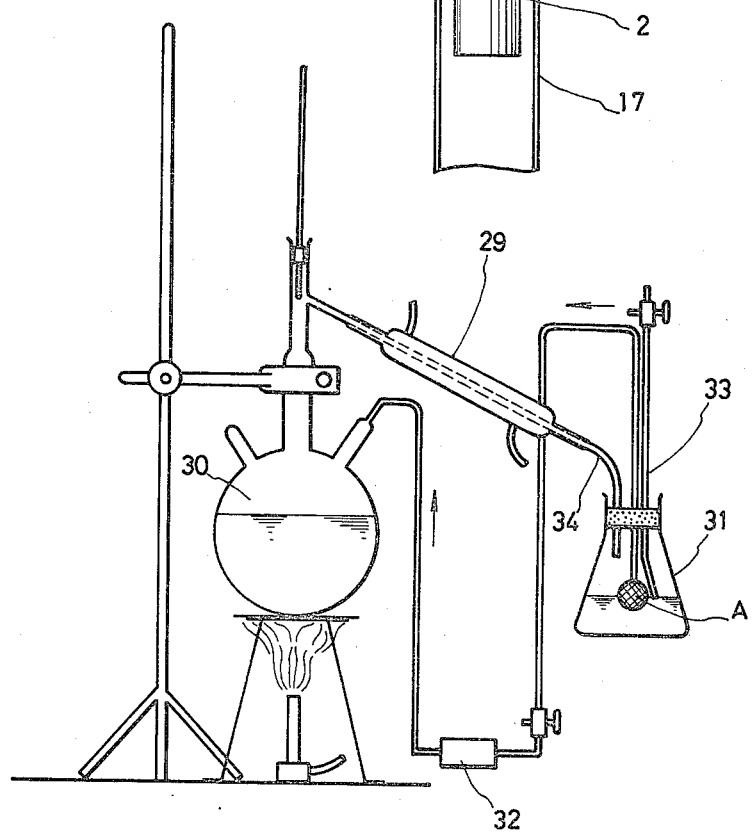

FILTER MEDIUM, PROCESS FOR PREPARATION THEREOF, FILTERING METHOD AND FILTERING APPARATUS

BACKGROUND OF THE INVENTION (1) Field of the Invention

The present invention relates to a filter medium having such an unexpectedly excellent effect that clogging of the filter medium with a filter cake is not caused at all and the filtration can be performed at a substantially uniform flow rate throughout the operation, and the present invention relates also to a process for preparing this filter medium and a filtering method and apparatus using this filter medium.

By the term "filtration" used in the instant specification is meant an operation of separating at least one component from a dispersion, and by the term "filter medium" is meant a member having a function or mechanism of separating at least one component from a dispersion. Further, by the term "filtering apparatus" used in the instant specification is meant an apparatus for separating at least one component from a dispersion by using a filter medium.

(2) Description of the Prior Art

In conventional filter media or filtering methods, as is well-known, a material to be treated by filtration (the term "dispersion" is used to avoid the confusion in the terminology) is contacted with a filter medium having a great number of small holes, and when the dispersion passes through the filter medium, a substance having a size larger than the mesh size of these small holes is left on the surface of the filter medium, but a substance having a size smaller than the mesh size of the small holes and a liquid (often referred to as "dispersion medium") are allowed to pass through these small holes, whereby filtration or separation is accomplished. During this filtering operation, clogging is inevitably caused more or less and sooner or later in the filter medium, and finally, filtration becomes difficult or extreme reduction of the efficiency is caused. In an extreme case, filtration becomes impossible.

A method in which the efficiency is enhanced by compression or suction is not different from the above-mentioned basic method in connection with the principle of filtration or separation. According to this method, only the filtration speed can be elevated, and in some case, clogging takes place rapidly.

When a porous material such as an unglazed plate or sponge or a material consisting of roughly, three-dimensionally and irregularly entangled wires is used as a filter medium, the filtration principle is the same as described above, and clogging is similarly caused.

In case of conventional filter media such as a filter paper and a filter cloth, dispersed phases having a larger size are first caught on holes of the filter medium, and with advance of the filtration, dispersed phases having a smaller size are caught on holes of the filter medium, the size of which has been reduced by the already caught dispersed phases. Thus, dispersed phases having a smaller size are gradually caught on the filter medium. As a result, precise filtration becomes possible. This means, however, that clogging already takes place in the filter medium, and therefore, the filtration speed is gradually reduced and finally, it becomes impossible to continue the filtration operation.

It is known that a so-called filter aid can be used for eliminating this disadvantage. However, even if such filter aid is used, the principle of filtration is the same as described above, and only a large quantity of a dispersion is treated by increasing the filtering area. In this case, the quantity of the dispersion that can be treated is in proportion of the amount of the filter aid used, and therefore, the filtration operation becomes expensive. The filter aid to be incorporated in a dispersion medium consists of particles and voids among these particles act as the above-mentioned holes. Accordingly, when such voids are clogged by a dispersed phase and the degree of clogging is appropriate, the intended precise filtration can be attained and this desirable state can be maintained. However, when the size of particles of the dispersed phase is fine, if clogging is advanced so as to cope with this fine particle size, it is impossible to maintain the fine dispersed phase and the filtration efficiency is inevitably reduced rapidly.

There has been proposed a filter medium comprising a net-like structure composed of three-dimensionally and irregularly entangled linear members such as wires and an effluent pipe connected to this net-like structure to cause a filtrate to flow out therefrom.

Also in this filter medium where linear members are merely entangled three-dimensionally and irregularly to form a net-like structure, as in case of conventional filter media, a filter cake composed of a dispersed phase is intruded into voids in the interior of the net-like structure, and when the particle size of the dispersed phase is small, the dispersed phase is allowed to pass through the net-like structure and no filtering effect can be attained.

SUMMARY OF THE INVENTION

It is a primary object of the present invention to provide a filter medium which has a filtration principle quite different from the above-mentioned filtration principle in the conventional filter media and in which the abovementioned inherent defect involved in the conventional filter media can be eliminated and clogging by a filter cake is not caused at all, and which has such a surprising property that the filtration can be performed at a substantially constant speed throughout the operation (this operation state is called "the constant and steady operation state" in the instant specification) and can be used repeatedly.

Another object of the present invention is to provide a filter medium in which a filter cake does not adhere to the body of the filter medium in the constant and steady operation state and before the filter cake arrives at the body of the filter medium, the separated dispersion medium (filtrate) becomes interposed between the filter cake and the body of the filter medium, whereby the filtration can be advanced while maintaining a high filtration precision.

Still another object of the present invention is to provide an epoch-making filter medium in which even a dispersed phase composed of particles having a size smaller than the size of voids of the body of the filter medium can be caught and separated from the dispersion medium.

A further object of the present invention is to provide a process for preparing a filter medium having such high capacity.

A still further object of the present invention is to provide a filtering method and apparatus in which the constant and steady operation state can be maintained effectively.

Other objects and advantages of the present invention will be apparent from the detailed description given hereinafter.

In accordance with the present invention, the foregoing objects can be attained by a filter medium comprising a body of the filter medium having the space thereof partitioned three-dimensionally, irregularly and manifoldly by bent linear members having a strength sufficient to cause substantially no deformation when the filter medium is actually used, thereby to form voids through which a dispersion medium as a filtrate is allowed to pass, and an effluent pipe connected to the body of the filter medium, said effluent pipe having an opening located in the interior of the body, from which a filtrate flows out, wherein the surface portion of the body of the filter medium has no substantial contact with a filter cake and the dispersion medium as the filtrate separated before the filter cake arrives at said surface portion, becomes interposed between the filter cake and the surface portion of the body of the filter medium, whereby the dispersion medium as the filtrate is allowed to flow from the surface portion to the opening of the effluent pipe located in the interior of the body of the filter medium at a substantially uniform flow rate.

In the filter medium of the present invention, linear members of the surface portion of the body of the filter medium may be knotted together to form a net-like structure on the surface. Alternately, another net-like structure may be disposed on the surface portion of the body of the filter medium to cover the surface.

The filter medium of the present invention having the above-mentioned structure may be prepared by collecting or gathering randomly around an opening of an effluent pipe linear members having a strength sufficient to cause substantially no substantial deformation when actually used, so that the space is partitioned three-dimensionally, irregularly and manifoldly by the linear members and the opening of the effluent pipe is located in the interior of the partitioned space, compressing the so formed body of a filter medium to bend the linear members, and fixing the bent linear members to the effluent pipe.

According to another embodiment, the filter medium of the present invention can be prepared by collecting or gathering randomly around an opening of an effluent pipe linear members having a strength sufficient to cause no substantial deformation when actually used, so that the space is partitioned three-dimensionally, irregularly and manifoldly by the linear members, compressing the collected or gathered linear members so that the linear members are bent in the state where the opening of the effluent pipe is located in the interior of the partitioned space, and covering the so formed body of a filter medium with a net-like structure substantially uniform in the mesh size.

When at least one component is filtered or separated from a material to be treated by filtration a dispersion by using the filter medium of the present invention, it is important that a dispersion medium as the dispersion medium is flowed into the filter medium in advance and filtration is started in the state where the filter medium is filled with the dispersion medium as the filtrate. When the filtration is carried out without any abrupt change being given to the flow rate of the filtrate, the constant and steady operation state can be effectively maintained.

In practising the filtering method of the present invention, the filter medium may be used as it is, but it is possible to dispose one or more filter media in a filtering tank or to charge the filter medium into a vessel filled with a dispersion. It is also possible to perform the filtration by utilizing the dynamic head of a dispersion or by using a filtration system comprising the filter medium connected to a suction device, a pressing device or the like member. Furthermore, it is possible to adopt a method in which the filter medium is submerged deeply in water and the filtration is carried out by utilizing the hydraulic pressure.

The mechanism or principle of filtration according to the filter medium of the present invention is quite different from that of filtration according to conventional filter media.

For better illustration of an unexpected filtration capacity of the filter medium of the present invention, characteristic properties of the filter medium of the present invention will now be described.

(a) The filtration speed is extremely high, and dispersions heretofore regarded as being unfilterable can be filtered. The flow rate is hardly changed throughout the filtration operation and the filtration can be performed at a substantially uniform rate. In short, the constant and steady operation state can be attained throughout the filtration operation. Accordingly, the filtering capacity of the filter medium of the present invention is much higher than the filtering capacities of conventional filter media and comparison based on numerical values will be impossible.

(b) An area necessary for the filtration can be remarkably reduced as compared with conventional filter media, and the filter medium of the present invention can be manufactured at a very low cost.

(c) Clogging is not caused at all. More specifically, when a filter cake present in the vicinity of the body of the filter medium is removed after completion of the filtration, any filter cake as the dispersed phase is not found intruding in "eyes" of the body of the filter medium (voids defined by linear members; since they seem as if they were eyes, these voids are often called "eyes"), and even if the body of the filter medium is broken and the interior is examined, no filter cake is present in the interior of the body of the filter cake. Since the filter cake does not intrude into the eyes or the interior of the body of the filter medium, the filter medium can be used repeatedly.

(d) When an emulsion is passed through the filter medium, the emulsion state is disorganized. As in the case of the system including a solid as the dispersed phase, the constant and steady operation state is attained and even a classifying phenomenon is observed. Accordingly, also in case of an emulsion, a peculiar phenomenon of the present invention that the filtration advances without any filter cake being left adherent to the surface of the body of the filter medium is similarly caused.

(e) The filter medium has a so-called classifying action. Namely, particles having a size exceeding a certain level are retained on the filter medium, but particles having a size smaller than such critical size are allowed to pass through the filter medium of the present invention. In case of an emulsion, the emulsion state is partially disorganized by this classifying action.

(f) The filter medium can retain not only the dispersed phase having a size larger than that of the "eyes" but also the dispersed phase having a size smaller than that of the "eyes" completely. By the term "retaining" is meant to prevent particles of the dispersed phase from adhering to the body of the filter medium and intruding into the interior of the body of the filter medium. This is one of important features of the filter medium of the present invention.

(g) In the same filter medium according to the present invention, the higher is the flow rate, the finer dispersed particles can be retained. This is another important property of the filter medium of the present invention, and by virtue of this property, the filtration precision and the operation efficiency can be improved. In case of an emulsion, elevation of the flow rate results in complete disorganization of the emulsion state.

(h) The above property means that clogging of the "eyes" is not caused at all in the filter medium of the present invention. In other words, the filter medium has a characteristic property that the dispersed phase does not adhere to the surface of the filter medium at all. This can be directly confirmed by the fact that when an emulsion is passed through the filter medium, a band of a transparent liquid is observed around the surface of the filter medium.

Since this effect is caused by the passage of the liquid through the filter medium, when a dispersion medium same as the filtrate obtained by the filtration is passed through or impregnated in the filter medium in advance and the filtration of the dispersion is initiated while the dispersion medium covers the filter medium, the filtration can be accomplished while maintaining the constant and steady operation state. Also by virtue of this characteristic feature, the filtration precision and efficiency can be improved according to the present invention, and hence, the above feature is one of important features of the present invention.

(i) When the body of the filter medium of the invention is covered with other net-like structure, the above characteristic properties are remarkably enhanced and the above-mentioned effects can be attained more smoothly.

Accordingly, even if the same filter medium is used for filtration of the same dispersion, the utility of the effects attained by the filter medium is varied to some extent depending on the mesh size of the net-like structure covering the filter medium. Especially in connection with the classifying action, the range of the constant and steady operation concerning the flow rate is narrower than in case of filtration of the transparent liquid. Accordingly, a higher classifying effect is attained when the filter medium is covered with a net-like structure.

(j) The above-mentioned fact holds good even if the phase reversion is caused between the dispersion medium and the dispersed phase. For example, when an oil is dispersed in water, the oil (floating) is obtained as an equivalent to the filter cake, and when water is dispersed in an oil, water (sedimented) is obtained as an equivalent to the filter cake.

(k) Not only a liquid having a low viscosity but also a liquid having a high viscosity such as a machine oil or a gelatin solution can be used as the dispersion medium conveniently. Further, not only crystalline substances but also materials that have been regarded as being unfilterable, such as aluminum hydroxide (precipitated gel), activated sludge or other bacterial colonies, ground meat pieces, sand or soil suspensions, fibers, deposited sludge, sewage, materials having a wide particle size distribution, e.g., ground vegetables and emulsions (disorganized emulsions) can be used as the dispersed phase conveniently in the present invention. According to the present invention, any of these materials can be effectively filtered while exerting the above-mentioned characteristic properties.

(1) Since a filter cake is not allowed into the interior of the body of the filter medium, it can be used repeatedly.

BRIEF DESCRIPTION OF THE DRAWING

FIG. 3-(B) is a front view illustrating the filter medium of FIG. 3-(A) covered with a net-like structure;

FIG. 9-(b) is an enlarged sectional view showing the connecting portion in the filter medium of FIG. 9-(a);

FIG. 10-(b) is an enlarged sectional view showing the connecting portion in the filter medium of FIG. 10-(a);

FIG. 12-(b) is a front view illustrating still another embodiment of the filter medium of the present invention;

FIG. 16 is an enlarged sectional view showing the filtering zone in the apparatus of FIG. 15;

FIG. 17 is a view showing an embodiment of the filtering apparatus in which filtration is carried out in the midway of chemical reaction.

DETAILED DESCRIPTION OF THE PREFERRED EMBODIMENTS

Figure 1:
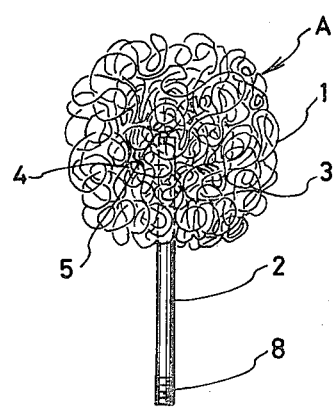
FIG. 1 is a front view illustrating one embodiment of the filter medium of the present invention.

Referring to FIG. 1, a filter medium A consists essentially of a body 1 composed of linear members 3 and an effluent pipe 2 having an opening 5 located in the interior of the body 1. The body 1 is constructed so that it has voids 4 formed by partitioning the interior space three-dimensionally, irregularly and manifoldly by bent linear members 3 having a strength sufficient to cause no substantial deformation when the filter medium is actually used and the filtrate is allowed to pass through these voids in the form of turbulent flows. The surface portion of the body 1 has a substantially uniform structure, and the voids 4 include not only clearances but also larger convexities or concavities and larger clefts. The opening 5 of the effluent pipe 2 is located substantially at the center of the spherical body 1, and it is preferred that the effluent pipe 2 be substantially closely contacted with the body 1. This condition means that any void or clearance larger than the voids 4 of the body 1 is not present between the body 1 and the effluent pipe 2. Other member such as a pipe may be interposed between the body 1 and the effluent pipe 2. The end portion of the effluent pipe 2 in the embodiment shown in FIG. 1 is threaded so that it can be connected to other member. For example, other means such as a socket may be disposed at the end of the effluent pipe 2 instead of such screwing threads.

When a dispersion is filtered by using the filter medium A having the above-mentioned structure, the filtrate as the dispersion medium is allowed to pass through the voids 4 of the body 1 and guided to the opening 5 of the effluent pipe 2. A filter cake as the dispersed phase is gathered to the vicinity of the body 1 together with the dispersion medium, but since the dispersion medium promptly separated is located in the surface portion of the body 1, the filter cake is prevented from closely adhering to the body 1. This is one of peculiar structural characteristics of the filter medium of the present invention, and by virtue of this structural characteristic, the constant and steady operation state can be maintained in the filter medium of the present invention.

Figure 2:
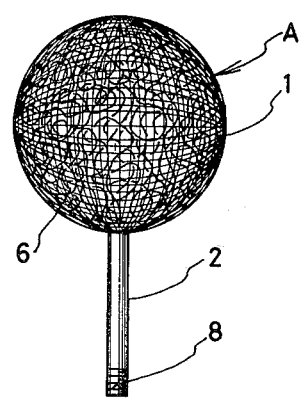
FIG. 2 is a front view illustrating the filter medium of the present invention covered with a net-like structure.

FIG. 2 is a view illustrating another embodiment of the filter member A in which the surface of the body 1 is covered with a net-like structure 6. In this embodiment, by the presence of this covering net-like structure, the deviation of directions of flows is reduced.

Figure 3:
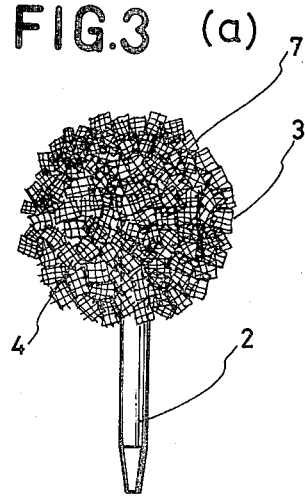
FIG. 3-(A) is a front view illustrating another embodiment of the filter medium of the present invention.
Figure 3:
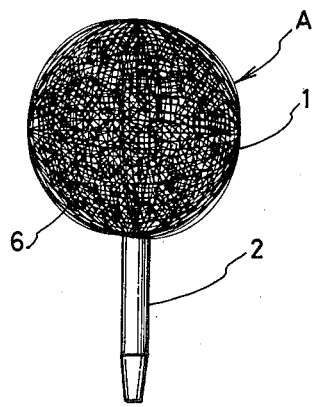

FIG. 3-(a) is a view illustrating a spherical body 1 formed by finely cutting a stainless steel net composed of linear members 3 and accumulating the resulting net pieces 7, and FIG. 3-(b) is a view illustrating an embodiment in which the spherical body shown in FIG. 3-(a) is covered with a net-like structure 6 to prevent falling-out of the net pieces 7 and reduce the deviation of directions of flows.

The linear member that is used in the present invention may be a long member such as a wire or a short member formed by cutting a wire. Further, the linear member has a coil-like shape or a chain-like shape or it may be composed of rings connected to one another. Although the kind of the linear member that can be used in the present invention, there are ordinarily used linear members composed of metals and of various fibers, for example, mineral fibers such as asbestos fibers, vegetable fibers such as kapok fibers, animal fibers such as wool fibers, inorganic fibers composed of glass, metals and rocks, synthetic fibers composed of polyesters, polyamides and the like, regenerated fibers and semi-synthetic fibers. When the filter medium of the present invention, it is necessary to maintain the constant and steady operation state throughout the filtration operation. For this purpose, the linear member should have a strength sufficient to cause no substantial deformation when the filter medium is actually used. From this viewpoint, it is preferred to use a linear member composed of a metal. Of course, even a linear member which is deformed under the actual filtration conditions is included in the scope of the present invention, if it is reinforced sufficiently by covering the body of the filter medium with a net-like structure or fixing appropriately connecting points of linear members.

The sectional shape of the linear member is not particularly critical but optional. For example, linear members having a circular, oval, rectangular or other polygonal sectional shape, and linear members having a modified shape thereof in the section.

The size of the linear member is changed depending on the kind of the dispersion and the state of the dispersion, and it is difficult to determine a certain range in connection with the size of the linear member. A linear member having an arc-like configuration or a bent linear member is advantageously used in the present invention.

The body of the filter medium of the present invention has a three-dimensional structure. For example, the body has a spherical configuration such as a configuration of a ball or spheroid, an oval configuration or a semi-globular configuration, or it has a configuration of a polyhedron such as a cube or rectangular parallelepiped (a polyhedron having many facets is included in the sphere). Of course, the configuration of the body of the filter medium is not limited to those mentioned above, and any of other appropriate configurations may be adopted.

In the present invention, the filtrate is introduced to the opening of the effluent pipe. In order to maintain the constant and steady operation state most effectively for this introduction of the filtrate, it is preferred to use a body of the filter medium having a spherical configuration or a configuration of a polyhedron having many facets. A body having a configuration of a globe is most preferred.

In the body of the filter medium of the present invention, linear members are accumulated and connected to one another very complicatedly and irregularly to form a three-dimensionally irregular net-like structure having voids allowing passage of a filtrate as the dispersion medium. The size of these voids is also determined according to the kind of the dispersion to be filtered, but in general, it is preferred that the size of the voids be 1 to 10,000 times, especially 1 to 1,000 times, the average size of the linear members, though the size of the voids is not particularly limited within such range in the present invention.

The body of the filter medium of the present invention may have an irregular structure entirely from the surface portion to the interior, or the irregular structure may include a hollow portion. Further, the body of the filter medium may have a structure comprising a plurality of layers in which the size of voids is increased toward the opening. Moreover, the body of the filter medium includes two or more kinds of linear member differing in, for example, the size, e.g., linear members of metal fibers and linear members of glass fibers.

Still further, the body of the filter medium in which linear members are connected to one another in the surface portion or in which connecting points of linear members are fixed by welding or fusion bonding or by means of an adhesive can be used effectively.

The body of the present invention may be covered with a dismountable or fixed net-like structure. The net-like structure is composed of a material which is not substantially deformed under the actual filtering conditions, such as a metal, a synthetic resin or a glass fiber. In order to eliminate the deviation of the flow rate or flow direction, it is preferred to use a net-like structure having a mesh size as uniform as possible. For the reasons described above with respect to the voids in the body of the filter medium, it is very difficult to fix definitely the mesh size of the net-like structure.

Figure 4:
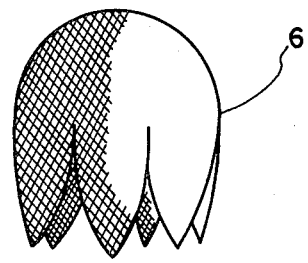
FIG. 4 is a perspective view illustrating one embodiment of the net-like structure to be used for the filter medium of the present invention.

FIG. 4 is a perspective view showing one embodiment of such net-like structure 6. A spherical body of the filter medium is filled in this net-like structure 6 and the open portion of the net-like structure is then closed.

Figure 5:
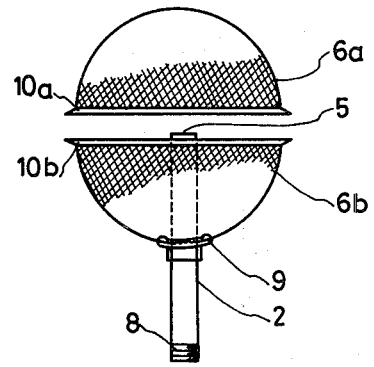
FIGS. 5 and 6 are front views illustrating another embodiments of the net-like structure.
Figure 7:
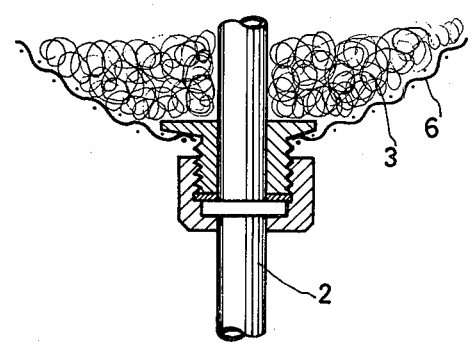
FIG. 7 is a sectional view illustrating one embodiment of connection of the net-like structure to the effluent pipe in the filter medium of the present invention.

FIG. 5 is a front view illustrating another embodiment of the net-like structure that is used in the present invention. In the embodiment shown in FIG. 5, semi-globular net-like structures 6a and 6b are combined into one globular structure. Edges 10a and 10b of the net-like structures 6a and 6b are integrated by welding, pressing or other means or by using an appropriate connecting member. The net-like structure 10b is fixed by the effluent pipe 2 and a washer 9. The net-like structure 10b may be fixed by welding or by using other appropriate member such as a screw. In an embodiment shown in FIG. 7, the net-like structure 6 and effluent pipe 2 are fixed together by means of a screw.

Figure 6:
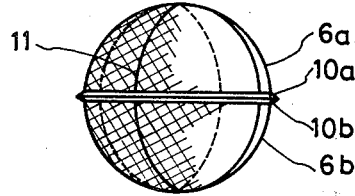

In an embodiment shown in FIG. 6, the semi-globular net-like structures 6a and 6b are combined together, and they are reinforced by other linear members having a high strength, such as metal wires 11.

It is preferred that large concavities and convexities or large clefts other than voids formed among linear members or between the linear members and the net-like structure be not present in the surface portion of the body of the filter medium.

Figure 8:
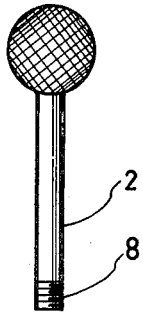
FIG. 8 is a front view illustrating one embodiment of the effluent pipe.

In the filter medium of the present invention, one end of the effluent pipe on the side having the opening is attached in the interior of the body of the filter medium, and the opening is located in the interior of the body of the filter medium. The position of the opening in the interior of the body is not particularly critical, but it is most preferred that the opening of the effluent pipe be located substantially at the center of the body of the filter medium. The effluent pipe is composed of a synthetic resin such as polyvinyl chloride or a metal. The opening of the effluent pipe may have an as-cut section of the pipe, or a net or porous material may be present in the opening according to need. More specifically, the opening of the effluent pipe may have a flat or curved face including a plurality of holes having a size allowing passage of the filtrate. If desired, the opening of the effluent pipe may be covered with a spherical net-like structure as shown in FIG. 8.

The principle or mechanism according to which the above-mentioned unexpected characteristic properties (a) to (k) can be attained in the filter medium of the present invention having the above-mentioned structure has not been completely elucidated, but from results of the experiments made by us and from unexpected phenomena confirmed at these experiments, which will be described hereinafter, it is construed that in the filter medium of the present invention, filtration will probably be accomplished according to the mechanism described below.

As pointed out hereinbefore, the constant and steady operation state can be maintained throughout the filtration operation according to the present invention. From this fact, it must be noted that the filtration mechanism in the present invention is apparently different from the filtration mechanism in conventional filter media such as filter papers, which has been explained in the beginning of the instant specification.

One of special phenomena confirmed by us, which will be described in Examples given hereinafter, is as follows:

When a dispersion is treated by using a filter medium as shown in FIG. 2, the dispersion medium in the dispersion is taken out of the body of the filter medium through the opening of the effluent pipe. The dispersed phase, i.e., the filter cake, in the dispersion is gathered toward the body of the filter medium but it is prevented from having close substantial contact with the body of the filter medium, and a layer of the dispersion medium is always interposed between the body of the filter medium and the filter cake. It is construed that this layer of the dispersion medium acts as a special site. Under these conditions, the filter cake does not intrude in the interior of the body of the filter medium and therefore, clogging is not caused at all. Further, the gathered filter cake is accumulated in the form of such a layer that the dispersion medium can pass therethrough most easily. Such special site is lost when the surface state is destroyed by violent agitation or the like.

The unique filter medium of the present invention may be prepared, for example, according to the following method.

Figure 9:
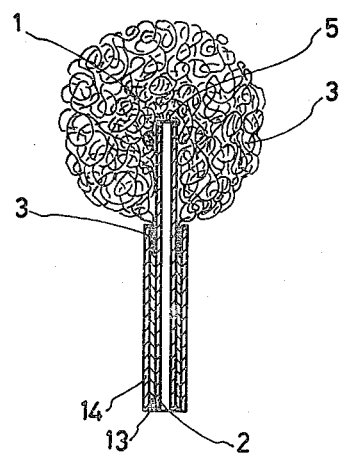
FIG. 9-(a) is a sectional view illustrating another embodiment of the filter medium of the present invention.
Figure 9:
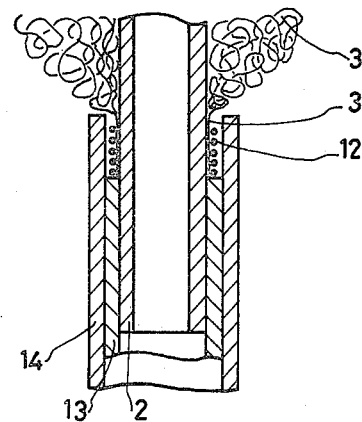

FIGS. 9-(a) and 9-(b) are given to illustrate one embodiment of the method for preparing the filter medium of the present invention. Linear members 3 are randomly collected around the periphery of an opening 5 of an effluent pipe 2 to form a temporary body of the filter medium. Then, the temporary body is compressed so that the linear members 3 are bent, whereby a body 1 of the filter medium is formed. Some linear members 3 present in the vicinity of the effluent pipe 2 are fixed to the effluent pipe 2 by means of metal wires 12 or the like. This fixing may be accomplished by optional means such as welding or by using an adhesive. The order of the compression step and fixing step is not particularly critical, and the fixing step may be conducted first. According to need, pipes 13 and 14 may be attached to the effluent pipe 2.

Figure 10:
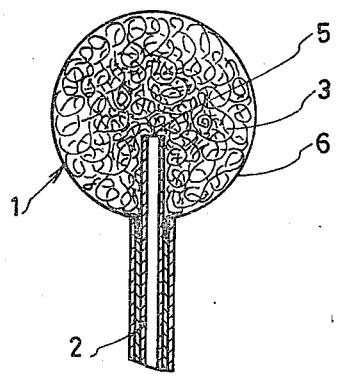
FIG. 10-(a) is a sectional view illustrating another embodiment of the filter medium of the present invention.
Figure 10:
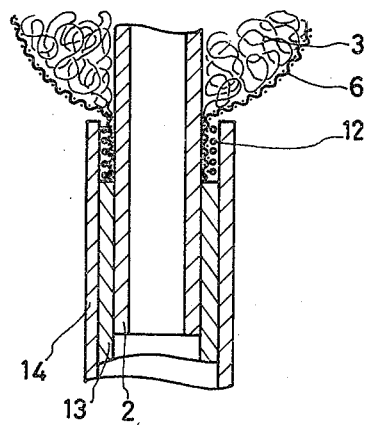

Referring to FIGS. 10-(a) and 10-(b) which are given to illustrate another embodiment of the method for preparing the filter medium of the present invention, linear members 3 are collected randomly around an opening 5 of an effluent pipe 2, and in the state where the space is partitioned three-dimensionally, irregularly and manifoldly and the opening 5 of the effluent pipe 2 is present in the interior of the thus partitioned space, the gathered linear members 3 are compressed so that they are bent, and the so formed body of the filter medium is covered with a net-like structure having a uniform mesh size. Some linear members 3 present in the surface portion of the body of the filter medium and located in the vicinity of the effluent pipe 2 are fixed by metal wires 12 or the like so taht they are interposed between the effluent pipe 2 and the net-like structure 6. According to need, pipes 13 and 14 may be attached to the effluent pipe 2.

It is preferred that the body of the filter medium be compressed so that large convexities or concavities or large clefts are not formed by compression. From this viewpoint, it is preferred that the body of the filter medium be compressed in the state covered with the above-mentioned net-like structure 6 or other net-like member. The linear members 3 can be fixed to the net-like structure constituting the surface portion according to need by welding or other means.

Formation of the body of the filter medium may be accomplished by collecting linear members in a liquid such as water to by randomly gathering spiral linear members and connecting them to one another. Compression is preferably performed at that the opening of the effluent pipe is located substantially at the center of the body of the filter medium and large convexities or concavities or large clefts are not formed. The net-like structure 6 may be formed by combining 2 semi-globular net-like structures 6a and 6b as shown in FIG. 5, and one of the net-like structures 6a and 6b may be composed of a liquid-impermeable material such as a film.

When a dispersion is filtered by using the filter medium of the present invention, it is preferred tha the body of the filter medium be impregnated with a dispersion medium which is to be separated as the filtrate or the filter medium be flowed through the body of the filter medium prior to initiation of the filtration operation. Namely, it has been found that the special effects of the present invention are attained when the fluid passes through the filter medium of the present invention. More specifically, prior to introduction of the dispersion, only the dispersion medium is impregnated in or passed through the body of the filter medium, and then, the dispersion is contacted with the filter medium in which the above-mentioned peculiar effects have already been exerted. If the dispersion is contacted with the filter medium without preliminarily including the dispersion medium in the body of the filter medium, filtration is performed according to the same principle as in conventional filter media, and occasionally, a state similar to the constant and steady operation state referred to in the present invention can be attained since also the dispersion medium passes through the body of the filter medium. However, the dispersed phase intrudes into the body of the filter medium while filtration is conducted according to the same filtration principle as in conventional filter media, and the presence of the dispersed phase intruding into the body of the filter medium distrubes the specific structure of the filter medium of the present invention. Accodingly, if the amount of such dispersed phase increases over a level allowing restoration of the original function of the filter medium, since ordinary filtration is further continued in this state, clogging is caused in the filter medium sooner or later. Further, when the restoration is incomplete, even if the constant and steady operation state is retained, no satisfactory results can be obtained with respect to the filtration precision and efficiency.

In the filtering method of the present invention, a dispersion comprising a plurality of components can be classified. Allowable ranges or conditions of the respective structural elements of the filter medium of the present invention for the classification are relatively limited, and therefore, a filter medium suitable for a certain dispersion can be easily found and the filtration can be performed with improved precision and efficiency by utilizing the classifying action. In a dispersion having a broad particle size distribution range, properties of particles should naturally differ. For filtration of such dispersion or a dispersion including a variety of particles differing in the particle-constituting material, it is required to perform filtration by utilizing the classifying action and find out a filter medium having a high classifying action.

According to the present invention, as illustrated in detail in Examples given hereinafter, a suitable filter medium is selected according to a dispersion to be actually filtered after due consideration of the following characteristic features of the present invention; namely, the effects are uniformalized in the vicinity of the body of the filter medium, the effects attainable can be changed minutely by adjusting the size of the voids or the mesh size of the net-like structure, and the effects are influenced by differences of the structures of the filter medium and the body of the filter medium.

The singularity of the filtration according to the present invention can be understood from the fact that as the flow rate is higher, even finer particles can be retained on the filter medium. Namely, the effect of maintaining the constant and steady operation state is exerted even on finer particles when the flow rate is increased. In case of a dispersion including active carbon as the dispersed phase, if a suspension once formed by classification in the constant and steady operation state is further filtered by using the same filter medium while increasing the flow rate, a transparent filtrate can be obtained by the constant and steady operation. Such dispersion can also be filtered by combining a plurality of filter media in which the mesh size of the net-like structure is gradually reduced.

Accordingly, in practising the filtering method of the present invention, an appropriate flow rate is chosen depending on the kind of the dispersion to be filtered. The flow rate can be adjusted or controlled by compression or suction. In order to maintain the constant and steady operation state effectively, it is preferred that no abrupt change of the flow rate be brought about in the filtrate and a flow rate as uniform as possible be attained. For the same reason, it is preferred that no extreme agitation be given to the dispersion. When filtration is carried out in a continuous manner as in the case where a dispersion to be filtered is poured into a filtration tank, it is preferred not to bring about such state that the dispersion impinges violently against the filter medium. For this purpose, a baffle board may be dispersed in the filtering apparatus or the position for pouring the dispersion is appropriately set.

When the filtration is carried out according to the present invention, it is desired to prevent the body of the filter medium of the present invention from falling in contact with the wall of the filtering equipment, the ground or other substance, because it is thereby made possible to reduce the filtration area and maintain the constant and steady operation effectively. There may be adopted an arrangement in which the filter medium is charged into a filtering tank from the upper portion thereof and a filtrate is taken out from the upper portion of the filtering tank through the effluent pipe. Namely, the effluent pipe is guided above the liquid level of the dispersion and the filtrate is recevered from above the liquid level of the dispersion.

In practising the filtering method of the present invention, a known filter aid capable of catching the dispersed phase as the filter cake and facilitating the passage of the dispersion medium through the filter cake may be added to a dispersion to be filtered. In case of a filter cake having a high flow resistance, when such filter aid is incorporated, it is possible to prevent reduction of the flow rate by the deposited filter cake.

The unexpected effect attained by the present invention can readily be understood from the fact that even a component having a size smaller than the size of the voids of the body of the filter medium or the mesh size of the net-like structure covering the surface of the body of the filter medium can be retained and separated as the filter cake, and hence, it will readily be understood that the filtration principle of the present invention is quite different from the filtration principle in the conventional filtration techniques. According to the present invention, for example, water or oil can be filter and separated from a mixture of water and oil which has been agitated very strongly, and moreover, the emulsion state can be disorganized in an emulsion containing a surface active agent to separate the emulsion into water and oil.

As pointed out hereinbefore, systems that cannot be filtered according to the conventional techniques can be effectively filtered according to the present invention, and the filed to which filtration is applicable can be remarkably boradened according to the present invention. Moreover, according to the present invention, it is possible to separate a reaction product or unreacted reactant while continuing a chemical reaction, whereby the reaction efficiency can be elevated and occurrence of a secondary side reaction can be prevented. The application fields of the filtration according to the present invention will be described in detail hereinafter.

The filter medium of the present invention may be used singly, or one filter medium or a plurality of filter media may be disposed in a vessel filled with a dispersion to be filtered. The body of the filter medium of the present invention or the net-like structure-covered body of the filter medium of the present invention may be covered with another net member or the like dismountably attached, whereby the adaptability of the filter medium to the repeated use can be remarkably enhanced. Even if the filtration per se is carried out promptly, when the dispersion medium is left in the filter cake, it is very difficult to remove the dispersion medium from the deposited filter cake by compression thereof, and if the deposited filter cake is compressed, a part of the filter cake is caused to intrude into the body of the filter medium and its function is lost. According to this preferred embodiment of the present invention, the filter medium is taken out and separated from the covering net member or the like, and compression filtration is carried out on the so left net member or the like, whereby the dispersion medium in the filter cake can be effectively squeezed out. In this manner, in the present invention, the adaptability of the filter medium to the repeated use can be remarkably enhanced by utilizing compression filtration.

Figure 11:
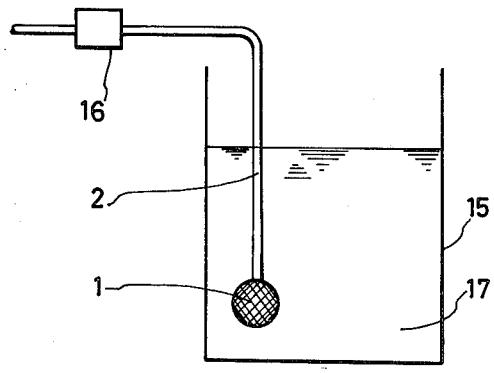
FIG. 11 is a sectional view illustrating one embodiment of the filtering apparatus according to the present invention.
Figure 12:
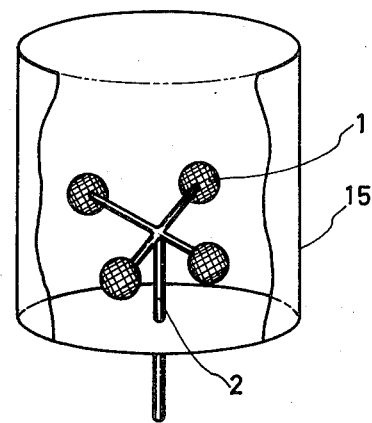
FIG. 12-(a) is a partially cut-out perspective view showing another embodiment of the filtering apparatus.
Figure 12:
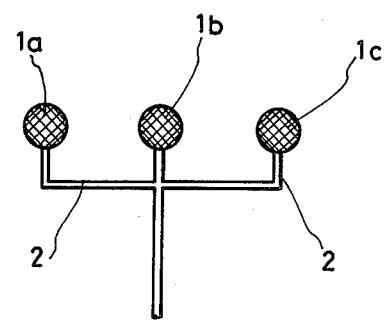
Figure 13:
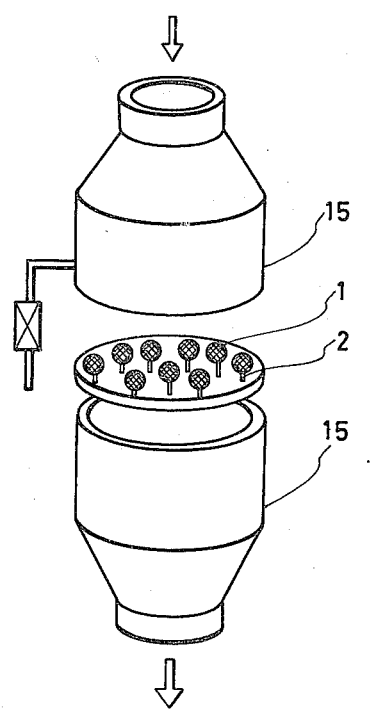
FIG. 13 is a disassembled view showing another embodiment of the filtering apparatus to the present invention.
Figure 14:
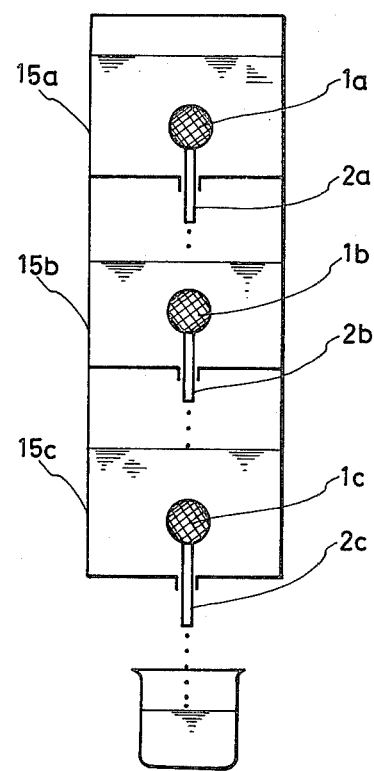
FIG. 14 is a sectional view showing another embodiment of the filtering apparatus according to the present invention.

As shown in FIG. 11, in the filtering apparatus of the present invention, the body 1 of the filter medium is submerged in a dispersion 17 in a filtering tank 15, and a filtrate is taken out above through the effluent pipe 2 by means of a pump 16. Further, as shown in FIG. 12-(a), the effluent pipe 2 may be extended to the outside from the lower portion of the filtering tank 15. Moreover, a plurality of bodies 1 may be disposed in the filtering tank 15. In an embodiment of the filter medium illustrated in FIG. 12-(b), a plurality of bodies 1a, 1b and 1c of the filter medium are connected to the effluent pipe 2. In FIG. 13, a plurality of the filter media comprising the body 1 and the pipe 2 are arranged in the tank 15. In an embodiment shown in FIG. 14, a plurality of filter media, each consisting of the body and the effluent pipe, are arranged in series, in which the filtration efficiency can be increased and the classification can be accomplished very effectively. In the embodiment shown in FIG. 14, the dispersion is first filtered by the body 1a in the filtering tank 15a, and the filtrate is introduced into the filtering tank 15b through the effluent pipe 2a. Then, the filtrate is filtered by the bodies 1b and 1c in succession.

When a plurality of filter media are disposed, they may be of the same kind, or they may differ in the internal structure, configuration, size and voids. These filter media may be connected in parallel or radially by means of pipes. Further, filtering tanks, each including a filter medium, may be connected in succession through effluent pipes. In this case, filter media differing in the kind may be disposed in the filtering tanks, respectively.

A device for adjusting the flow rate by suction or compression is attached to the filtering apparatus. The flow rate is changed so as to attain an optimum filtering capacity as pointed out hereinbefore, and further, when a filter cake happens to intrude into the interior of the body of the filter medium, the flow rate-adjusting device is operated to increase the flow rate to wash away the intruding filter cake.

According to the present invention, unexpected results can be obtained in various fields for collection, separation and purification of a variety of substances, and the present invention is effectively applied to chemical reactions, water treatments, sewage treatments and emulsion-disorganizing treatments. Further, when the filtering method of the present invention is applied to manufacture of a variety of products, effects of improving the quality, increasing the manufacturing rate, increasing the yield, reducing the manufacturing cost, saving the labor expenses and diminishing the equipment site. As a result, technical developments which have heretofore been regarded as being difficult can be attained by utilization of the present invention, and therefore, the present invention is very significant from the industrial viewpoint. Examples of actual applications of the present invention are described below.

Recovery of valuable substances from oils such as waste oils.

Separation of waste waters from gasoline stands and other plants into water and oil and purification of these waste waters.

Exploitation of crude oils of the water-in-oil and oil-in-water types.

Maintenance and improvement of capacities of machines such as oil-impregnated vacuum pumps by perpetual filtration of oils.

Smooth supply of oils to boilers, automobiles, petroleum fuel stoves, air-crafts, internal combustion engines, ships, etc.

Recovery of effluent oils.

Prevention of flow-out of oils in various ships.

Simplification of the steps in the process of manufacturing edible oils such as rape oil and sesame oil.

Simplification of the steps and increase of yields in manufacture of beam jam, mashed and sweetened sweet potatoes, sweet bean jelly, bean curd and other cakes.

Filtration of coffee, cocoa and the like.

Simplification of the steps in manufacture of cheese, butter, cream and other dairy products.

Treatment of waste waters discharged from sinks, washing machines, baths, other household machines, etc.

Purification of waters of ponds, moats, pools, etc. and maintenance of clarity in these waters.

Purification of highly contaminated waste waters discharged from restaurants, hotels, halls and fish markets.

Filtration of activated sludges.

Filtration of sludges and similar deposits.

Removal of corruptions from industrial waters used repeatedly in iron mills, power plants and other flowback machines.

Collection of fish eggs and laver sprouts and other utlizations to ocean culture.

Purification of dranking water by removal of active carbon or the like.

Cleaning of manholes.

Collection of mineral substances and ores in mines and stone pits and purification of waste waters discharged therefrom by filtration.

Filtration of sludges deposited in bottoms of harbors and rivers.

Purification of sea water and river water and recovery of valuable substances therefrom.

Purification of liquids in water supply systems and liquid transportation systems by filtration.

Collection of fruit juices.

Utilization to manufacture of refrigerants and carbonated drinks.

Improvement of the quality of soups and canned foods.

Selection of particle sizes of sands for concrete.

Utilization to formation of tablets of aspirin, penicillin and other medicines.

Improvement of the quality of china, porcelain and other ceramic products.

Simplification of the steps in manufacture of soy sauce, sugar, sodium glutamate and other seasonings and increase of yields thereof.

Utilization to manufacture of brewages such as sake, beer and wine, distilled liquors such as shochu (low-class distilled spirits), brandy and whisky, and fermentation products such as butanol.

Utilization to manufacture of paper, pulp, fumaric acid and fructose.

Utilization to the sewage treatment.

Utilization to manufacture of coloring materials, pencils, inks, black writing liquids and other writing materials and treatment of waste waters discharged from plants of manufacturing them.

Treatment of waste waters discharged from plants to preparing aluminum sashes, glass-manufacturing plants and plating plants.

Utilization to manufacture of cosmetic and ointment bases such as lard and vaseline.

Extraction of animal and vegetable components such as natural rubber, pine oil, whale oil and cod-liver oil.

Utilization of conversion of sea water to fresh water.

Utilization to analytic chemistry, for example, treatment of the intended product dissolved out in thin layer chromatography.

Application to P.H. type devices for measuring automatically oxygen consumption and other measuring devices and machines, for example, improvement of the measurement accuracy by covering an electrode with the filter medium.

Utilization to manufacture of amino acids and peptides such as glycine, taurine, aspargic acid, aspargic acid amide and glutathione.

Utilization to photographic industries using films and printing sheets.

Utilization of manufacture of industrial acid and alkali chemicals such as sulfuric acid, hydrazine, acetic acid and oxalic acid.

Utilization to manufacture of inorganic industrial chemicals such as sodium sulfate, sodium hydrogencarbonate, bleaching powder and borax.

Utilization of manufacture of fertilizers such as calcium nitrate, ammonium sulfate, urea and potassium carbonate.

Utilization to manufacture of agricultural chemicals such as urbazid, Bordeau mixture and sugamycin hydrochloride.

Utilization to manufacture of organic industrial chemicals such as ethanol, phenol, cresol and aniline.

Utilization to manufacture of plasticizers such as diheptyl phthalate, dioctyl adipate and tricresyl phosphate.

Utilization of perfumes and refined oils such as anise oil, camellia oil, olive oil, white rose oil and bergamot oil.

Utilization to manufacture of coconut oil, sesame oil, oilve oil and other oils and fats.

Utilization to manufacture of detergents and surface active agents such as soaps and sodium dodecylbenzenesulfonate.

Utilization to manufacture of natural resins such as rosin, dammar and copal.

Utilization to manufacture of plastics such as vinyl chloride, polyvinyl chloride, polyethylene, polyacrylates, polyesters, epoxy resins, urethane resins, styrol resins and polypropylene.

Utilization to manufacture of synthetic rubbers and regenerated rubbers such as acrylic rubbers and oil-rubbers.

Utilization to manufacture of adhesives such as resorcine resins and silicone rubbers.

Utilization to manufacture of pigments such as lake red C, benzidine yellow and methyl violet lake.

Utilization to manufacture of paints such as oil paints, spirit varnishes and alkyd resins.

Utilization to manufacture of dyes such as Congo Red, Sumilan Green BL and Spirit Blue.

Utilization to manufacture of viscose rayon and acetate rayon fibers and synthetic fibers composed of polyethylene terephthalate, nylon-6,6 and other polymers.

Utilization of manufacture of solvents such as acetone, benzene, methanol, xylene, hexane, pyridine, tetrachloroethylene, polyethylene glycol and ethylene glycol.

Utilization to manufacture of rolling massage creams, vanishing creams, cold creams, lip sticks and other cosmetics.

Utilization to manufacture of explosives such as Carlit and dynamite.

Utilization to manufacture of formalin, naphthalene, p-dichlorobenzene and other insecticides.

Utilization to manufacture of synthetic materials such as acetylene, cyclohexane, acetaldehyde and monochloroacetic acid.

Utilization to manufacture of rouge, chlorophyll and other natural dyes.

Utilization to manufacture of saccharin, sugar and other sweetening agents.

Utilization to manufacture of antiobiotics such as penicillin, streptomycin, erythromycin, aureomycin and chloramphenicol.

Utilization to manufacture of disinfectants such as mercurochrome, iodoform and acrinol.

Utilization to manufacture of hormones and vitamins such as predonisone, progesterone, vitamin $B_1$, vitamin C and activated vitamin $B_1$.

Utilization to manufacture of herb medicines such as arrowroot starch gruel and

Utilization to manufacture of medicines such as antipyrene, barbital, procaine hydrochloride, diphenhydramine, scopolia extract, chlorpromazine, diastase, takadiastase, sulfamines, castor oil, magnesium sulfate, sulfur, hydrazine hydrochloride, chloroform, atropine sulfate, kainic acid, santonin, glucose, casein, powdered milk, condensed milk, iodine, effedrine, codeine phosphate, camphor, digitoxin, vitacampher, theophyllol, sodium thiosulfate, caffeine, adrenaline, pyrabital, ichthyol, ethyl aminobenzoate, morphia, heroin, methylpropamine, tubocurarine chloride and sodium p-aminosalicylate.

Utilization to manufacture of food additives such as sodium alginate, sodium phosphate, sodium 5'-guanylate, propylene glycol, sodium hydrogensulfite, alginine, benzoic acid, eugenol, aluminum chloride, citric acid, tartaric acid, glycerin, sodium chondroitin sulfate, lactic acid nicotinamide, alum, methionine, menthol and folic acid.

Utilization to manufacture of industrial chemicals such as ammonia, ammonium chloride, calcium carbamate, sodium sulfide, furon, carbon disulfide, calcium carbonate, coal tar, toluol, styrene monomer, naphthol, thinner, ethylene, acrylonitrile, fattu acids and hardened oils.

Utilization to manufacture of herbicides such as 2,4-dichlorophenoxyacetic acid.

Utilization to manufacture of fire extinguishers such as carbon tetrachloride.

Specific contents and peculiar characteristics of the present invention will now be described by reference to the following Examples that by no means limit the scope of the invention.

EXAMPLE 1

Spirals having a diameter of about 2 mm and a spiral pitch of about 5 to about 7 mm were formed from 25 g of a metal wire of count 30 according to JIS, and they were cut into pieces, each having a length of 3 to 6 cm. The cut pieces were collected around an opening of a JIS soft vinyl pipe having an inner diameter of 7 mm and a length of 8 cm. As shown in FIGS. 9-(a) and 9-(b), some cut pieces 3 were thinly wound around the vinyl pipe 2, and metal wires 12 were wound on the gathered cut pieces 3 and connected to fix the cut pieces 3. Then, a JIS soft vinyl pipe 13 having an inner diameter of 9 mm and another JIS soft pipe 14 having an inner diameter of 12 mm were embedded in the assembly as shown in FIGS. 9-(a) and 9-(b). The so formed body composed of entangled cut pieces was then covered with a net and compressed to have a substantially spherical shape about 6 cm in diameter. Then, the net was taken out from the compressed body. Thus, a filter medium A according to the present invention was obtained. In this filter medium, the body 1 was composed of irregularly and complicatedly entangled cut pieces (linear members) spaced by 1 to 7 mm from one another. The body 1 had such a strength that it was not deformed under normal filtration conditions.

No clefts were present in the surface portion of the so obtained filter medium, and the body of the filter medium and the effluent pipe were tightly fixed to each other. None of clearances having a size larger than that of the voids of the body of the filter medium were observed in the surface portion of the filter medium.

EXAMPLE 2

A filter medium was prepared in the same manner as described in Example 1 except that the metal wire was not cut but optionally bent. Another filter medium was prepared in the same manner as in Example 1 except that the spirals of the metal wire were not cut but wound on one another. In each of the so obtained filter media, no larger clefts were present in the surface portion.

EXAMPLE 3

A filter medium as shown in FIGS. 10-(a) and 10-(b) were prepared according to the following procedures.

In water, 0.5 g of glass filter paper fiber JIS GF1B was dispersed under agitation, and the dispersed fiber was gathered around an opening 5 of a glass effluent pipe 2 having an outer diameter of about 5 mm, an inner diameter of about 3 mm and a length of about 5 cm and was charged in a semi-globular polyvinyl chloride net 6 having a mesh size of 100 mesh and a diameter of about 2 cm, one end of which was opened in a columnar shape. Then, the columnar portion of the polyvinyl chloride net 6 was closed while slightly compressing the body 1 portion composed of the fiber, in such a manner that the opening 5 of the effluent glass pipe 2 was located substantially at the center of the body 1 and a very small part of the filter paper fiber 3 was substantially uniformly interposed between the effluent pipe 2 and the polyvinyl chloride net 6. Then, metal wires 12 were wound on the net 6 and connected to fix the assembly. When the glass filter paper fiber portion, namely the body, of the so prepared filter medium was examined by a magnifying glass, it was found that the body has a three-dimensional and irregular net structure.

EXAMPLE 4

Figure 15:
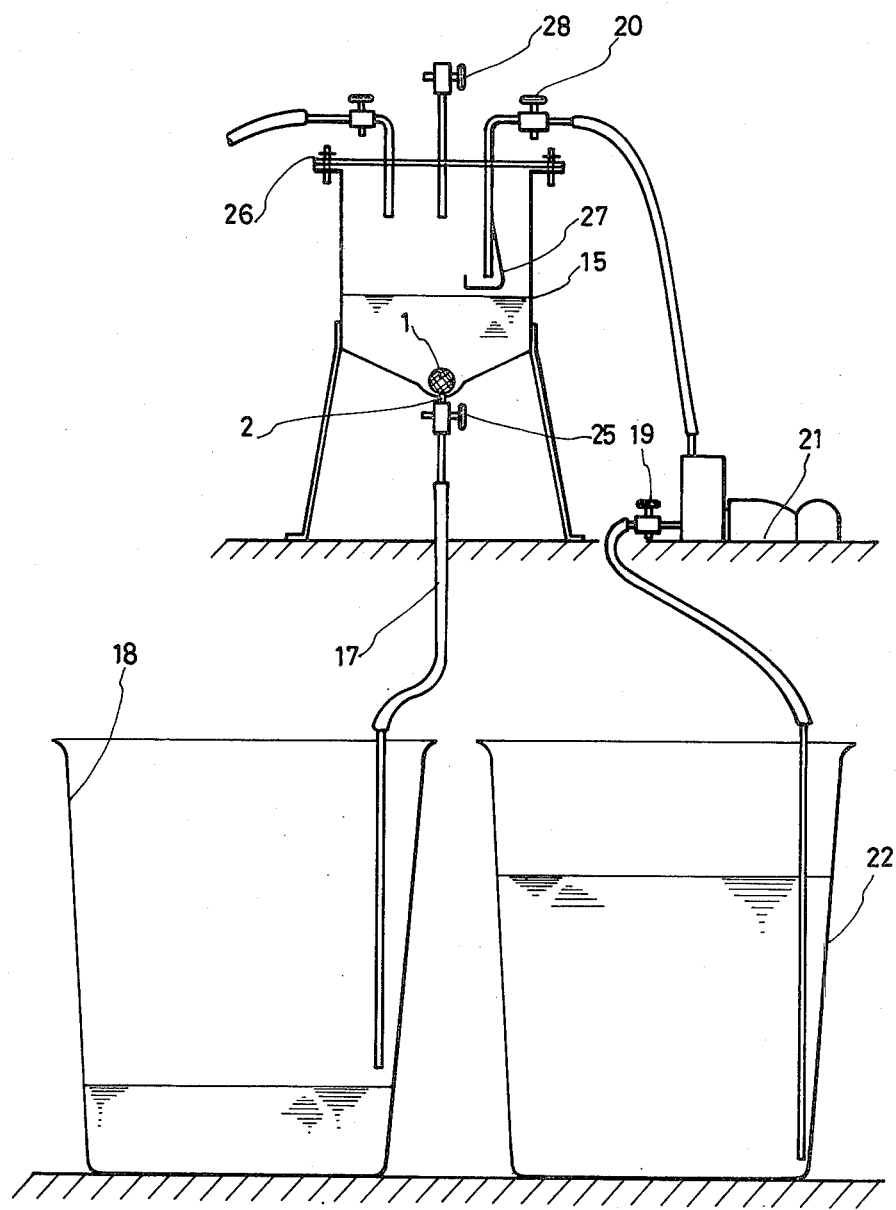
FIG. 15 is a systematic view showing still another embodiment of the filtering apparatus of the present invention.

A dispersion was filtered by using a filtering apparatus as shown in FIGS. 15 and 16.

The dispersion treated in this Example was one formed by adding slaked lime to a sewage stored in a sewage tank for receiving waste water discharged from a plant for extracting glycyrrizin from licorice, removing the formed precipitates, rendering the filtrate weakly acidic by addition of dilute sulfuric acid and adding active carbon (decoloring carbon) to the filtrate.

The filter medium used for the filtration was one prepared according to the method described in Example 3 by dispersing a glass filter paper fiber in water, gathering the dispersed fiber around an opening of an effluent pipe to form a substantially spherical body having a diameter of about 3.5 cm and covering the body with a polyvinyl chloride net having a mesh size of 100 mesh.

The filter medium was charged in a stainless steel filtering tank 15 having a capacity of about 20 l, and a valve 28 was opened to fill water in the tank 15 so that the body 1 of the filter medium was immersed in water to pass water through the filter medium. Then, water was transported to a tank 18 through a liquid transporting pipe 17. While the body 1 of the filter medium was impregnated with water, valves 19 and 20 were opened but the valve 28 was closed, and a pump 21 was operated to introduce the dispersion stored in a tank 22 into the filtering tank 15. When the flow rate was adjusted to 7 l/hr (reading on the pressure gauge being 0.01 Kg/cm$^2$), the constant and steady operation state was attained and all the dispersion was filtered in this state. This filtrate was seemingly transparent and had a very slight colloidal opacity. When the flow rate was adjusted to 22 l/hr (reading on the pressure gauge being 0.3 Kg/cm$^2$) in the above experiment, the constant and steady operation was attained and all the dispersion was filtered. The obtained filtrate was excellent over the above filtrate with respect to the transparency. When the flow rate was adjusted to 28 l/hr (reading on the pressure gauge being 0.9 Kg/cm$^2$), the constant and steady operation state was maintained and all the dispersion was filtered. The obtained filtrate was not opaque as compared with distilled water. When the flow rate was adjusted to 35 l/hr (reading on the pressure gauge being 1.3 Kg/cm$^2$), the constant and steady operation state was attained and all the dispersion was filtered. The obtained filtrate was as colorless and transparent as the filtrate obtained at the third experiment. The transparency of the filtrate obtained at the second experiment was comparable to the transparency of service water.

Each of the filtrates obtained at the above experiments could be discharged as colorless and transparent treated waste water.

In each of the foregoing experiments, the filter medium was impregnated with water in advance, and while water was retained in the filter medium, filtration was started. When the dispersion was passed through the filter medium directly without preliminary impregnation with water, because of clogging continuation of the filtration became substantially impossible in about 5 minutes under the conditions of the first experiment and in about 6 minutes under the conditions of the second experiment. Under the conditions of the third experiment, the filtrate obtained at a flow rate of about 20 l/hr was apparently more opaque than the filtrate obtained at the third experiment. Under the conditions of the fourth experiment, a filtrate substantially free of opacity was obtained at a flow rate of about 29 l/hr.

From the foregoing experimental results, it will readily be understood that the separation precision and efficiency can be remarkably improved in filtration of a dispersion including a liquid as a dispersion medium according to the present invention.

EXAMPLE 5

To 17.5 g of licorice produced in USSR (particle size distribution: from fine powder to 3×10 cm at largest) was added 120 l of water, and the mixture was allowed to stand overnight in the cold state and was then filtered by using a filter medium prepared in the same manner as described in Example 1 by using a metal wire of count 10 of JIS. The resulting slightly viscous suspension was filtered as the starting dispersion in the following manner.

(1) Filter Medium:

| Filter Medium | Material, Standard and Weight of Body | Diameter (cm) of Filter Medium | Effluent Pipe inner diameter (cm) | Effluent Pipe outer diameter (cm) | Mesh Size (mesh) of Covering Net |
| --- | --- | --- | --- | --- | --- |
| a | metal wire, 30 count, 30g | 6 | 1.2 | 1.5 | 14 |
| b | metal wire, 30 count, 30g | 6 | 1.2 | 1.5 | 80 |
| c | metal wire, 30 count, 30g | 6 | 1.2 | 1.5 | 150 |
| d | steel wool, 8g | 5 | 0.9 | 1.2 | 14 |
| e | " | 5 | 0.9 | 1.2 | 80 |
| f | " | 5 | 0.9 | 1.2 | 150 |
| g | glass fiber, 11g | 4 | 0.6 | 0.9 | 14 |
| h | " | 4 | 0.6 | 0.9 | 80 |
| i | " | 4 | 0.6 | 0.9 | 150 |

(2) Polyvinyl Chloride Pipe Used:

| No. | Inner Diameter (mm) | Outer Diameter (mm) |
| --- | --- | --- |
| 1 | 13 | 18 |
| 2 | 20 | 26 |
| 3 | 25 | 32 |

(3) Operation Method:

A filter medium comprising a body 1 of the filter medium and an effluent pipe 2 was disposed in a filtering tank 15 as shown in FIG. 16. In case of the filter media a to f, the effluent pipe 2 was inserted into the polyvinyl chloride pipe No. 1 as a liquid transporting pipe 17, and a rubber plate 23 was interposed and the effluent pipe 2 was fixed by a rubber thread 24. In case of the filter media g to i, the polyvinyl chloride pipe No. 2 was used as a liquid transporting pipe 17.

Referring to FIG. 25, the valve 25 was closed to fill water in the filtering tank 15, and the lid 26 was shut and sealed by a clamp. Then, a small quantity of water was filled in the tank 22, and valves, 19, 20 and 25 were opened but other valves were closed. The pump 21 was operated in this state. The valves were adjusted to maintain a predetermined pressure. Then, the pump 21 was once stopped, and water in the filtering tank 15 was reduced to such an extent that the body 1 of the filter medium and the baffle board 27 alone were immersed in water. Then, the starting dispersion was filled in the tank 22 and the pump 21 was operated again to perform the separation operation. Obtained results are shown below.

| Filter Medium | Operation Conditions | Attainment of Constant and Steady Operation State | Flow Rate at Constant and Steady Operation State | State of Filtrate | Remarks |
|---|---|---|---|---|---|
| a | — | not attained | — | — | *** |
| b | — | not attained | — | — | *** |
| c | 0.9 Kg/cm² | attained | 30 l/hr | suspended | * |
| d | 0.9 Kg/cm² | attained | 24 l/hr | suspended | ** |
| e | 0.9 Kg/cm² | attained | 24 l/hr | suspended | ** |
| f | 0.9 Kg/cm² | attained | 24 l/hr | suspended | ** |
| g | — | not attained | — | — | *** |
| h | — | attained | — | — | *** |
| i | — | attained | — | — | *** |

Note:
*: When the operation conditions were changed and the pressure was reduced (the flow rate was reduced), a filtrate having a slightly higher transparency was obtained (the constant and steady operation state was attained).
**: When the operation conditions were changed and the pressure was reduced, the opacity was slightly increased (the constant and steady operation state was attained).
***: No constant and steady operation state was attained when the pressure was in the range from a level close to atmospheric pressure (very low flow rate) to about 1.0 Kg/cm² pressurization.

When the filter medium of the present invention is used, the higher is the flow rate, even dispersed particles having a smaller size can be retained on the filter medium. If the size of the "eyes" of the filter medium of the present invention is made slightly larger, as the flow rate is lower, smaller dispersed particles can be retained. However, in the latter case, the allowance of the structural conditions for the filter medium showing the characteristic properties (dispersed particles having a size smaller than the size of the "eyes" of the filter medium can be retained and the constant and steady operation state can be attained) is remarkably restricted. In constrast, in the former case (the higher is the flow rate, even the smaller dispersed particles can be attained), the allowance of the structural conditions for the filter medium showing the characteristic properties is considerably broadened.

When the opaque filtrates obtained in the above experiments (opaque filtrates obtained by using the filter media c, d, e and f; the classification was conducted in these experiments) could be filtered at very efficiently while maintaining the constant and steady operation state by the use of the filter media g, h and i, and transparent filtrates, i.e., extracts, could be obtained.

As will be apparent from the foregoing experimental results, according to the present invention, the separation precision and efficiency can be remarkably improved in separation and filtration of a dispersion including a liquid dispersion medium.

The principle of the filtration separation in the present invention has not yet been elucidated, and this will be clarified by reasearches made hereinafter.

In the above Example 5, a dispersion including solids as the dispersed phase was treated. The separating effect of the present invention is manifested as disorganization of the emulsion state when a dispersion including a liquid as the dispersed phase, i.e., an emulsion, is treated. Also in this case, the above effects of improving the separation precision and efficiency can be similarly attained. In the above Example 5, the dispersion contained water as the dispersion medium. When an organic solvent such as an alcohol, a ketone, a petroleum fraction, an amine or an organic acid is a dispersion medium and for example, active carbon is a dispersed phase, the above effects of improving the separation precision and efficiency are more conspicuous than in case of a dispersion including water as the dispersion medium. Thus, the present invention includes a great number of embodiments of the methods and apparatuses for improving the separation precision and efficiency, and it is impossible to describe all of them one by one in detail. Furthermore, the present invention can be applied effectively to a great number of reactions which have not been practically worked because of difficulties involved in the filtration step and reactions which have not been practised because it is difficult to disorganize emulsions.

EXAMPLE 6

A glass fiber was strongly rubbed, and by using this glass fiber, a filter medium having a body having a radius of about 6 cm (the surface was covered with a polyvinyl chloride net having a mesh size of 1.2 mm × 1.2 mm) was prepared in the same manner as described in Example 3.

Water was passed in advance through the so prepared filter medium of the present invention, and when an aqueous dispersion of aluminum hydroxide gel or activated sludge was filtered by this filter medium, the constant and steady operation state was attained and the filtration was accomplished very effectively. When milk was filtered by this filter medium, the emulsion state was disorganized and cream was obtained as an equivalent to a filter cake. When a liquid formed by finely dispersing an oil in water was filtered by this filter medium, the oil was separated as an equivalent to a filter cake. Even if the filtration was carried out under compression or suction, the constant and steady operation state could be maintained as above.

EXAMPLE 7

This Example illustrates an embodiment in which the present invention is applied to the process for preparing isoamyl ether by dehydrating isoamyl alcohol with sulfuric acid. The reaction is expressed by the following reaction formula:

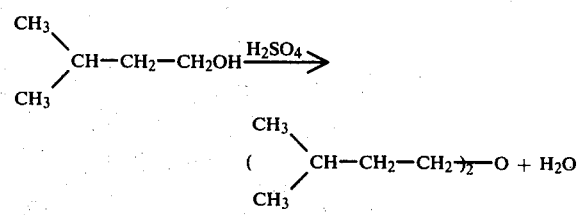

The filtering apparatus used was one shown in FIG. 17. Glass fibers cut into a length of 2 to 4 mm were dispersed uniformly in water so that an opening of an effluent pipe was located substantially at the center of a body of a filter medium to be formed. The dispersed glass fibers were compressed to have a substantially spherical shape having a radius of about 5 mm, whereby a three-dimensional and irregular net-like assembly was formed. The assembly was covered with a 80-mesh stainless steel net. The so formed filter medium was used.

The cock was opened to pass water into the cooling pipe 29, and the flask 30 charged with 600 ml of isoamyl alcohol and 60 g of concentrated sulfuric acid was heated. In a short time, the content of the flask was boiled and a suspended distillate was stored in the flask 31. When the filter medium A was covered with this distillate, the liquid feed pump 32 was operated, whereby a transparent liquid (isoamyl alcohol having a boiling point of 130° C.) was flowed into the reaction flask 30, and the volume of water left in the bottom of the flask 31 was increased. Occasionally, the glass pipe 33 was taken up so that the lower half of the filter medium A located near the top end of the glass pipe 33 was immersed in the surface portion of the distillate. When the reaction was advanced in this state, no fresh distillate was obtained any more in about 5 hours. Accordingly, the heating was stopped, and steam was blown into the reaction flask 30. The obtained distillate was distilled to obtain 275 g of isoamyl ether (having a boiling point of 172° C.).

EXAMPLE 8

This Example illustrates an embodiment in which the present invention is applied to the process for preparing palmityl anilide by reacting aniline with palmitic acid in xylene. The reaction is expressed by the following chemical formula:

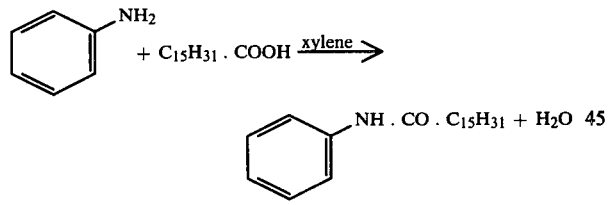

The filtration operation was carried out by using the apparatus shown in FIG. 17.

The reaction flask was charged with 256 g of palmitic acid, 350 g of aniline and 200 ml of xylene, and the content was boiled by heating. In a short time, an emulsified distillate was obtained in the flask 31 and it was separated into two layers. At this point, the liquid feed pump 32 was operated to flow transparent xylene (containing aniline) into the reaction flask 30 through the glass pipe. When the reaction was advanced by continuing heating, in about 1 hour, increase of the amount of water in the lower layer was not observed any more. At this point, heating was stopped, and an adaptor 34 was connected to an Erlenmeyer flask having an inner capacity of 1000 ml. Steam was blown into the reaction flask 30 to distill xylene and excessive aniline. With cooling, a large quantity of a white crystal was precipitated in the reaction flask 30. The crystal was collected, recrystallized from hot water and dried to obtain 323 g of palmityl anilide in the form of a white crystal having a melting point of 90° C.

As will be apparent from the foregoing illustration, when the filtering method of the present invention is adopted, the reaction product can be removed from the reaction system while continuing the reaction, the effects of shortening the reaction time, increasing the yield of the product and increasing the reaction efficiency remarkably can be attained.

EXAMPLE 9

Figure 18:
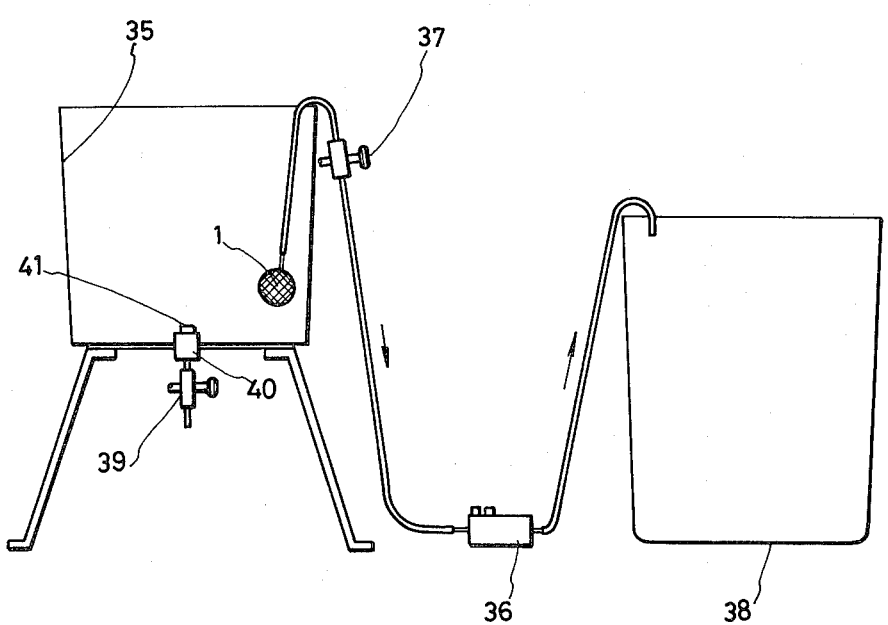
FIG. 18 is a view illustrating still another embodiment of the filtering apparatus according to the present invention.

A filter medium was prepared according to the method described in Example 3 by dispersing glass fibers cut into a length of 2 to 5 mm in water under agitation to form a spherical body having a diameter of about 3.5 mm around an effluent pipe, covering the surface of the body with a 14-mesh polyvinyl chloride net, and coating the upper half of the body close to the effluent pipe (opened substantially to the center of the body) with gypsum. The so formed filter medium was located in the middle portion of a filtering tank of the filtering apparatus shown in FIG. 18.

A machine oil for a vacuum pump was charged in the tank 35 and the pump 36 was operated to impregnate the body 1 of the filter medium in advance with the machine oil. A waste oil (opaque water-in-oil type emulsion) which had been used for a long time in an oil immersion type vacuum pump (used mainly for reduced pressure filtration of dispersions including water as the dispersion medium) and had an apparently reduced evacuating capacity was filled in an amount of about 5 l into the tank 35, and the liquid feed pump 36 was operated and the cock 37 was controlled to adjust the flow rate to about 0.5 l/hr. The constant and steady operation state was maintained and all the emulsion was disorganized by filtration. A transparent machine oil was fed to the tank 38 and 0.5 l of an opaque liquid composed mainly of water was left in the bottom portion of the tank 35. This liquid was discharged by opening the cock 39. The recovered machine oil obtained in the tank 38 was directly used for an oil immersion type vacuum pump and it was found that the same capacity at attainable by a fresh machine oil could be exerted by this recovered oil.

When the above experiment was conducted by using a filter medium having an effluent pipe extended downwards from the body of the filter medium, namely by disposing the above-mentioned filter medium at a position 41 of the top end of an effluent pipe 40 equipped with a cork 39, the waste oil flowed out substantially in the original state and the object of recovery of the machine oil could not be attained.

Incidentally, when it is intended to filter the above waste oil by using a filter cloth or filter paper, it is resident on the filter medium but any liquid does not flow out through the filter medium, or if the waste oil passes through the filter medium, the state of the filtrate is substantially the same as that of the starting waste oil.

As will be apparent from the foregoing illustration, the embodiment in which the effluent pipe is extended upwardly from the body of the filter medium is very effective for exerting the characteristic properties of the filter medium of the present invention according to properties of dispersions to be treated.

EXAMPLE 10

The filter medium used in this Example was prepared according to the method described in Example 1 in the following manner.

A metal wire having a diameter of about 0.5 mm was bent and entangled three-dimensionally, irregularly and manifoldly to form a body of a filter medium havina a spherical shape having a radius of about 2 cm (distances between every two adjacent wire pieces being about 1 to about 2 mm), and the top end of an effluent pipe having a diameter of about 1.5 cm and equipped with a Mohr cock in the midway thereof was located substantially at the center of a body. The so constructed filter medium was attached to a hole formed at the center of the bottom of a tank having a bottom diameter of about 16 cm and a height of about 20 cm. FIG. 1 illustrates only the filter medium of the present invention used in this Example. In the case of this filter medium, a similar view is obtained when the filter medium is cut along any optional section.

Wet pulverized licorice (having a particle size distribution range from fine powder to $3 \times 10$ mm at largest; 16 l of water was added to 2 Kg of pulverized licorice) was filtered with the above-mentioned filter medium through which water had been passed in advance. A transparent filtrate flowed out and all the wet pulverized licorice could be filtered in about 2.5 minutes from the point when the constant and steady operation state was attained.

EXAMPLE 11

Equal amounts of glass fibers formed by disentangling a glass fiber filter paper and ordinary glass fibers cut into a length of 2 to 3 cm were mixed in water, and the mixed glass fibers were gathered around the top end of an effluent pipe and formed into a body having a substantially spherical shape about 15 mm in the radius. The so formed assembly was filled in semi-globular net-like structures shown in FIG. 5 to obtain a filter medium.

When 200 ml of water was added to about 1 l of a machine oil and the mixture was violently stirred, and emulsion was formed. In order to disorganize the emulsion state, the liquid had to be allowed to stand for at least 1 week. When this dispersion was filtered by a filter paper, relatively large dispersed particles were removed, but the emulsion state was not disorganized.

The above filter medium of the present invention was sufficiently impregnated in advance with the above machine oil alone, and separation of the agitated emulsion was carried out in a tank by using the so impregnated filter medium. The effluent pipe was taken out to the outside from the upper portion of the tank and the top end of the effluent pipe was located at a level lower than the position of the bottom of the tank. A sucking device was connected to the top end of the effluent pipe to effect suction, and when the effluent arrived at the vicinity of the top end of the effluent pipe, the suction was stopped. Then, the filtration was conducted according to the principle of the siphon. The constant and steady operation state was attained and a transparent filtrate composed solely of the machine oil flowed out at a rate of about 200 ml/min, while water was left in the tank.

In the above experiment, an emulsion of the water-in-oil type was treated. The amounts of water and the oil were reversed in the emulsion and the filter medium was sufficiently impregnated with water in advance. Thus, the emulsion was filtered in the same manner as described above. Water flowed out from the effluent pipe and the emulsion was effectively separated into water and the oil. Thus, it was confirmed that an emulsion of the oil-in-water type can also be effectively separated according to the present invention.

What we claim is:

1. In a method for separating at least one filtrate from a dispersed phase using a filter medium comprising a body of the filter medium having the space thereof partitioned three-dimensionally, irregularly and manifoldly by bent linear members having a strength sufficient to prevent substantially any deformation when the filtrate flows therethrough, such that voids are formed wherein the filtrate passes through said voids, and an effluent pipe connected to the body of the filter medium and having an opening located in the interior of the body of the filter medium, the filtrate flowing out of said filter medium through said effluent pipes the improvement comprising, pre-impregnating said filter medium body with dispersed phase free filtrate such that said filter medium is completely immersed in said filtrate and thereafter feeding a flow of said filtrate with said dispersed phase therein towards the surface of said filter medium body so as to provide a constant and steady operation state wherein said filtrate continues to flow through said filter medium body and through said effluent pipe and said dispersed phase is formed around said filter medium body but separated therefrom with the filtrate interposed between the dispersed phase and the surface of the filter medium body.

2. A method according to claim 1 wherein abrupt changes are not caused in the flow rate of the filtrate by hydraulic head suction or liquid face compression but a substantially uniform flow rate is maintained.

3. A method according to claim 1 wherein a component having a size smaller than that of the voids of the body of the filter medium is separated as the filter cake.

4. A method according to claim 1 wherein at least one component is separated from a mixture or emulsion including at least two incompatible liquids.

5. A method according to claim 1 wherein classification is effected by increasing the flow rate by compression or suction, and/or by gradually diminishing the size of the voids of the surface portion of the body of the filter medium, and/or by covering the surface portion of the body of the filter medium with a net-like structure of varying mesh size.

6. A method according to claim 1 wherein a reaction product or unreacted reactant is separated as the filtrate while conducting a chemical reaction.

7. A method as set forth in claim 1 wherein said filter medium body has a spherical shape, thereby enhancing the uniformity of flow therethrough.

* * * * *